(12) United States Patent
Takanashi

(10) Patent No.: US 6,491,428 B1
(45) Date of Patent: Dec. 10, 2002

(54) X-RAY COMPUTED TOMOGRAPHY APPARATUS

(75) Inventor: Tetsuyuki Takanashi, Yaita (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 82 days.

(21) Appl. No.: 09/649,178

(22) Filed: Aug. 29, 2000

(30) Foreign Application Priority Data

Aug. 30, 1999 (JP) .......................................... 11-243856

(51) Int. Cl.[7] .......................... H01J 35/10; H01J 35/12
(52) U.S. Cl. ....................................... 378/200; 378/199
(58) Field of Search .................... 378/200, 4, 130, 378/141, 199; 165/244

(56) References Cited

U.S. PATENT DOCUMENTS

| 4,918,714 A | 4/1990 | Adamski et al. ............ 378/121 |
| 5,588,482 A | * 12/1996 | Holka ......................... 165/44 |
| 5,761,269 A | * 6/1998 | Sugihara et al. ............. 378/199 |

FOREIGN PATENT DOCUMENTS

JP 6-38795 5/1994

* cited by examiner

Primary Examiner—Robert H. Kim
Assistant Examiner—Courtney Thomas
(74) Attorney, Agent, or Firm—Oblon, Spivak, McClelland, Maier & Neustadt, P.C.

(57) ABSTRACT

An X-ray computed tomography apparatus including a rotor rotated in a predetermined direction, an X-ray tube unit mounted on the rotor, an X-ray detector opposed to the X-ray tube unit to detect X-ray transmitted through a subject, and a radiator unit mounted on the rotor. The radiator unit includes a tubed casing, a radiator engaged with a frontal opening of the casing in an orientation in which the radiator is subjected to the air moved by rotation of the rotor at a substantial front face thereof, a circulating system configured to circulate a fluid between the X-ray tube unit and the radiator, and a radiator air exit opened at the rear of the casing. The radiator unit further includes a switch for opening and closing the radiator air exit.

16 Claims, 13 Drawing Sheets

X-RAY COMPUTED TOMOGRAPHY APPARATUS

CROSS-REFERENCE TO RELATED APPLICATIONS

This application is based upon and claims the benefit of priority from the prior Japanese Patent application No. 11-243856, filed Aug. 30, 1999, the entire contents of which are incorporated herein by reference.

BACKGROUND OF THE INVENTION

The present invention relates to an X-ray computed tomography apparatus in which an X-ray tube is cooled by coolant, for example oil or cooling water. This will be explained using the most popular oil as an example.

FIG. 1 shows a structure of a rotation section inside a gantry of a conventional X-ray computed tomography apparatus. A substantially annular rotor 77 is rotatably supported by a fixing section (not shown). This rotor 77 has X-ray tube unit 71 and an X-ray detector 76 mounted thereon. This X-ray tube utilizes a braking X-ray that is accelerated by a high voltage applied between a cathode and an anode and generated by causing collision with the anode at a very high speed. As well known, the conversion efficiency of the X-ray energy against electric energy is very low, and 99% or more of the electric energy is converted into a heat. When a focal face of the anode is excessively high, the anode material is fused, and cracks, resulting in shorter service life of the X-ray tube. In order to increase a heat capacity, an apparatus of such type housing an X-ray tube in a container together with insulation oil is mainly used at present. In addition, there is employed an apparatus of such type improving a cooling effect by forcibly circulating oil between the X-ray tube unit 71 and a radiator (core) 73 of a radiator unit 72.

Further, in helical scan which is significantly popular recently, it is required to general an X-ray within a comparatively long time and continuously. In addition, X-ray strength per a unit time is likely to increase in order to suppress lower sensitivity due to a higher rotation speed. In order to process the thus increased heat rate, it is required to provide a fan 74 for forcibly cooling oil. The ventilation capability of this fan 74 is very highly designed based on the maximum heat rate of the X-ray tube simulated under a severe scan condition.

Thus, an excessive cooling state can occur under a normal scan condition. This excessive cooling provides an environment in which arcing is likely to occur with thermal electrons inside of the X-ray tube.

In addition, the fan 74 having its very high cooling capability generates a very large operating noise. This operating noise not only causes discomfort to a patient and an operator, but also interferes voice communication between the patient and the operator.

BRIEF SUMMARY OF THE INVENTION

An object of the present invention is to reduce noise in an X-ray computed tomography apparatus, while ensuring the cooling effect of the X-ray tube.

According to the present invention, this apparatus comprises: a rotor rotated in a predetermined direction; an X-ray tube unit mounted on the rotor; an X-ray detector opposed to the X-ray tube unit to detect X-rays transmitted through a subject; a radiator mounted on the rotor; a circulating system configured to circulate and a fluid between the X-ray tube unit and the radiator. The radiator is disposed in a direction in which the radiator is subjected to the air moved by the rotation of the rotor at its front face.

According to the present invention, when the rotor is rotated, the radiator is subjected to the resultant air at its front face, whereby the fluid can be efficiently cooled. In addition, an air cooling fan is eliminated or the operation frequency of the air cooling fan can be reduced, and thus, noise can be significantly reduced.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Hereinafter, the present invention will be described in detail with reference to the accompanying drawings by way of preferred embodiments. Computed tomography apparatuses are classified into various types of apparatuses such as a rotate/rotate-type apparatus for integrally rotating an X-ray tube and X-ray detector around a subject and a stationary/rotate-type apparatus for rotating only an X-ray tube around a subject while a large number of detection elements are arranged in a ring. The present invention is applicable to any type and will be explained using the most popular rotate/rate-type apparatus as an example.

(First Embodiment)

Figure 1:
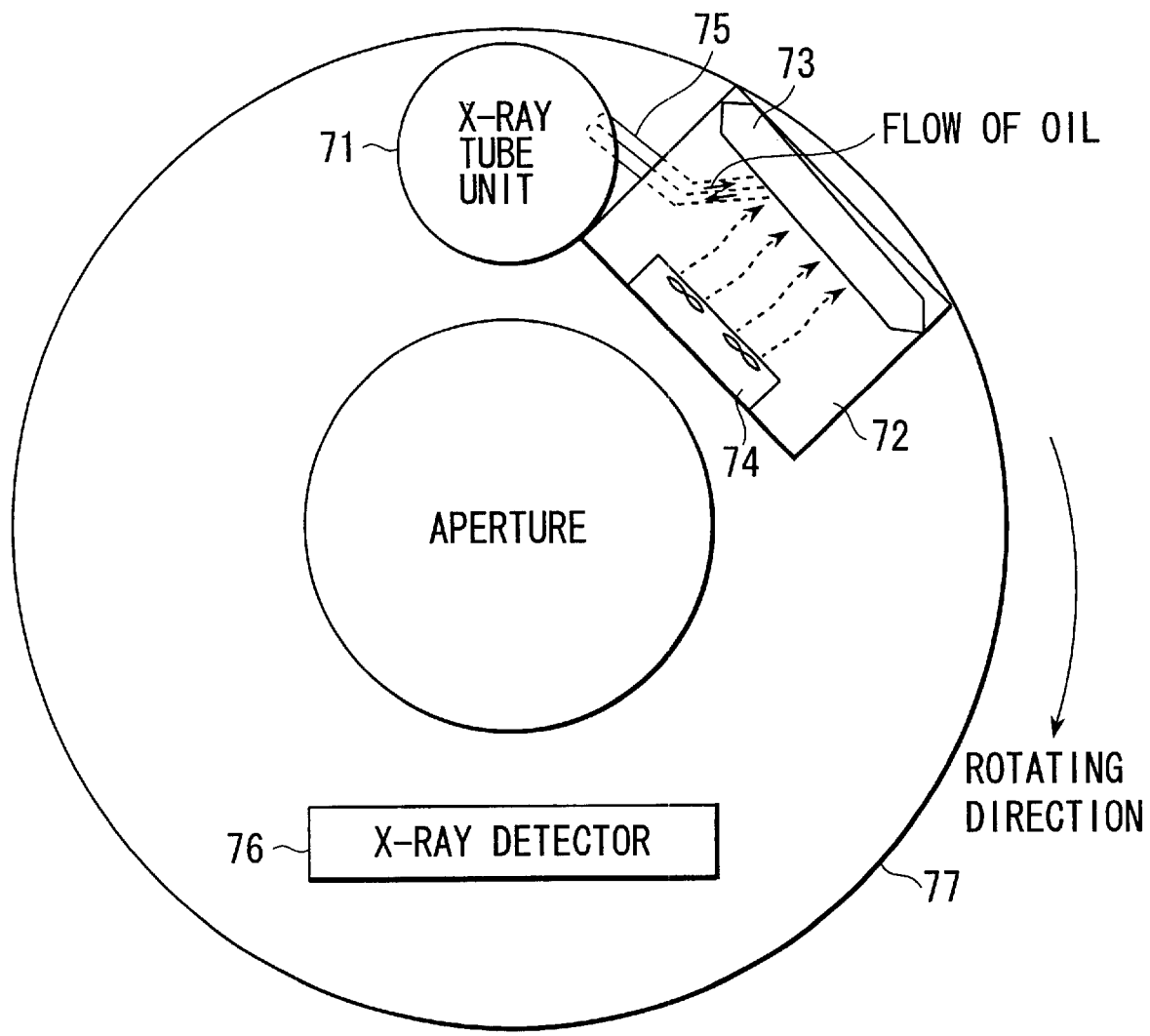
FIG. 1 is a structural view showing a rotation section inside of a gantry of a conventional X-ray computed tomography apparatus.
Figure 2A:
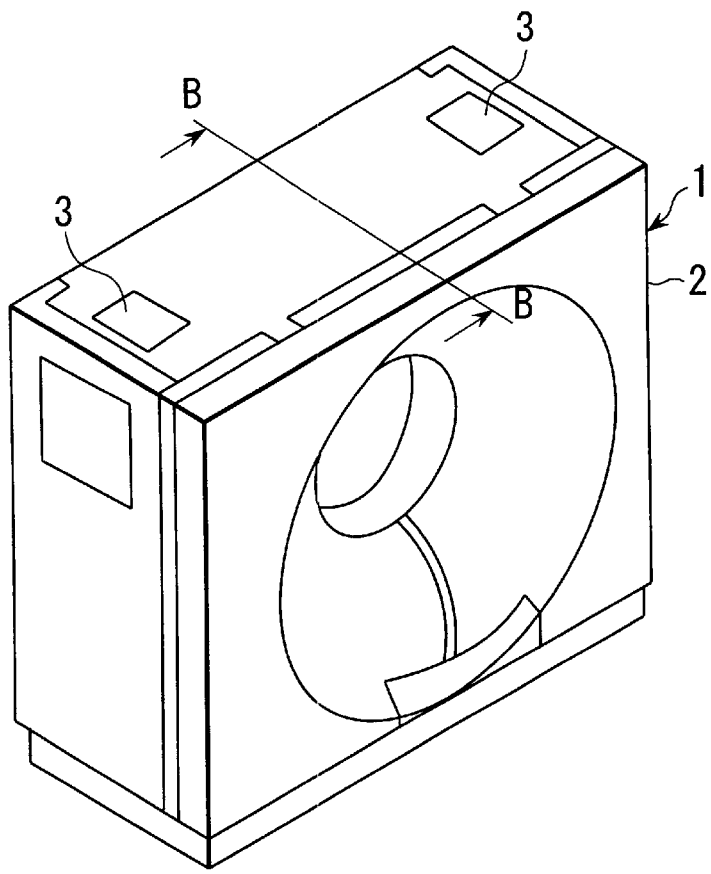
FIG. 2A is an external view showing a gantry of an X-ray computed tomography apparatus according to a first embodiment of the present invention.
Figure 2B:
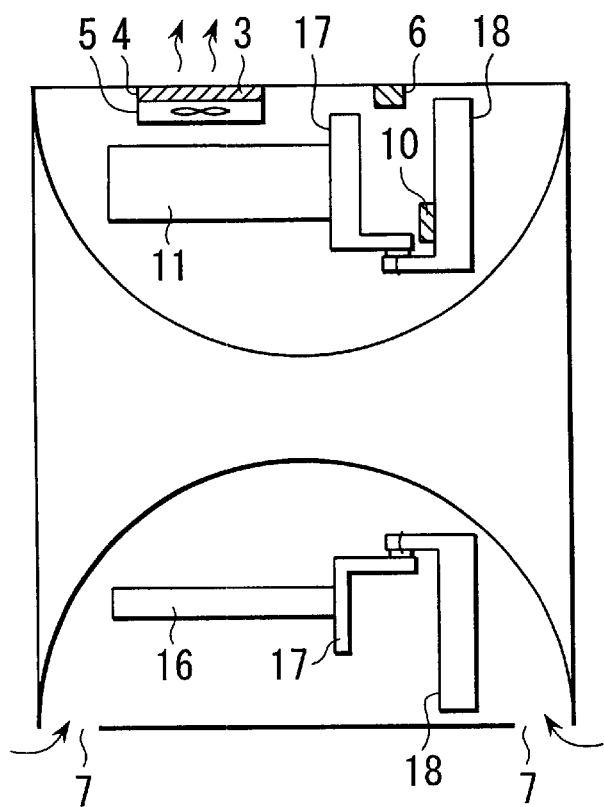
FIG. 2B is a sectional view taken along the line B—B of FIG. 2A.

FIG. 2A shows an appearance of a gantry of an X-ray computed tomography apparatus according to a first embodiment. FIG. 2B is a sectional view taken along the line B—B shown in FIG. 2A. A gantry 1 houses a number of parts in a cabinet 2. A rotor 17 is rotatably supported by a fixing frame 18. A direct drive motor, for example, is employed in order to rotate this rotor 17 at a high speed. An X-ray tube unit 11 for generating X-rays and an X-ray detector 16 for converting the X-rays transmitted through the subject examined into an electric signal are mounted on the rotor 17. The X-ray tube unit 11 is such type housing the X-ray tube together with coolant in the X-ray tube container. This invention will be explained using the most popular insulation oil as an example of the coolant.

In order to prevent the heat generated by the X-ray tube unit 11 from being accumulated inside of the cabinet 2, an exhaust port 3 is provided at the upper part of the cabinet 2, and a air intake port 7 is provided at the lower part of the cabinet 2. An electrically driven opening and closing mechanism 4 is mounted on this exhaust port 3 so that the exhaust port 3 can be opened and closed as required. When the exhaust port 3 is opened, the inside warmed up air is discharged from the exhaust port 3 to the outside. Instead, a new air is entered from the air intake port 7. In order to improve this ventilation efficiency, a ventilation fan unit 5 is mounted inside of the opening and closing mechanism 4. As will be described later in detail, activation of this fan unit 5 and opening and closing of the exhaust port 3 are controlled based on activation/deactivation of the rotor detected by a rotary encoder 10 mounted on a fixing frame 18.

Figure 3:
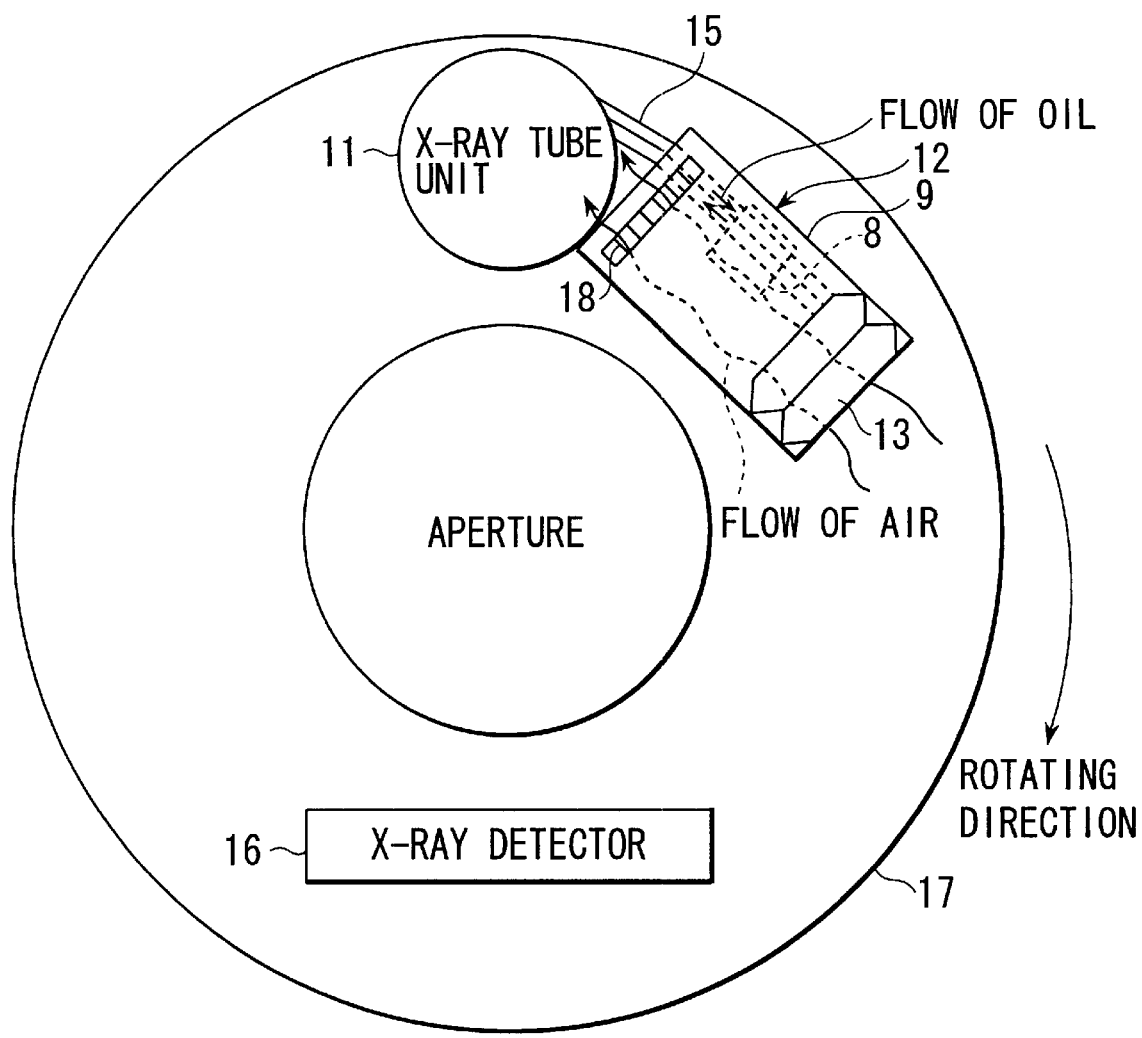
FIG. 3 is a structural view showing a rotation section inside of the gantry shown in FIG. 2A.

FIG. 3 is a front view showing the rotor 17 shown in FIG. 2B. At the rotor 17, the radiator unit 12 is mounted in addition to the X-ray tube unit 11 and the X-ray detector 16. This radiator unit 12 is disposed in the vicinity of the X-ray tube unit 11 and at a position which is more frontal than the X-ray tube unit 11 in the rotational direction of the rotor 17. A cabinet 9 of the radiator unit 12 is cylindrical, and a substantially flat shaped radiator (core) 13 provided with a heat radiating fin is engaged with an opening which is frontal thereof. An oil hose 15 is coupled between this radiator 13 and the X-ray tube unit 11, and the oil is circulated between the radiator and the X-ray tube unit 11 by means of a circulation pump 8.

The above radiator 13 is disposed so as to be substantially parallel to a tangent line at a position of the radiator 13 in a circle whose center is a rotary shaft of the rotor 17. By disposing the radiator 13 in such orientation, the air moved by rotation of the rotor 17 is subjected to the radiator 13 at its front, and the oil can be efficiently cooled. Therefore, an air cooling fan is eliminated or the operating frequency of the air cooling fan can be reduced, and thus, noise can be significantly reduced.

A radiator air exit 18 for exhausting the warm air passing through the radiator 13 is opened at the rear of the cabinet 9 of this radiator unit 12. This radiator air exit 18 is opened laterally rather than backwardly so as not to directly subject the warmed air through the radiator 13 to the X-ray tube unit 11. An air filter for removing dust or the like generated from a slip ring or the like is engaged with this radiator air exit 18.

Figure 4:
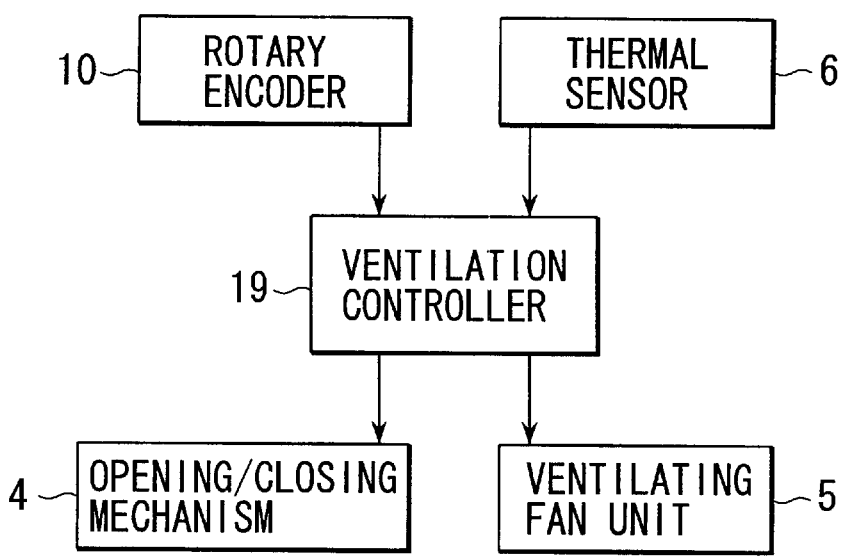
FIG. 4 is a block diagram showing a ventilation control system in the first embodiment.

FIG. 4 shows a control system for controlling opening and closing of an exhaust port 3 and activation/deactivation of a ventilation fan unit 5. A ventilation controller 19 controls opening and closing of the exhaust port 3 and activation/deactivation of the ventilation fan unit 5. This controlling is performed based on the cabinet inside temperature detected by the temperature sensor 6 as described above; and activation/deactivation of the rotor 17 detected by the rotary encoder 10.

Figure 5:
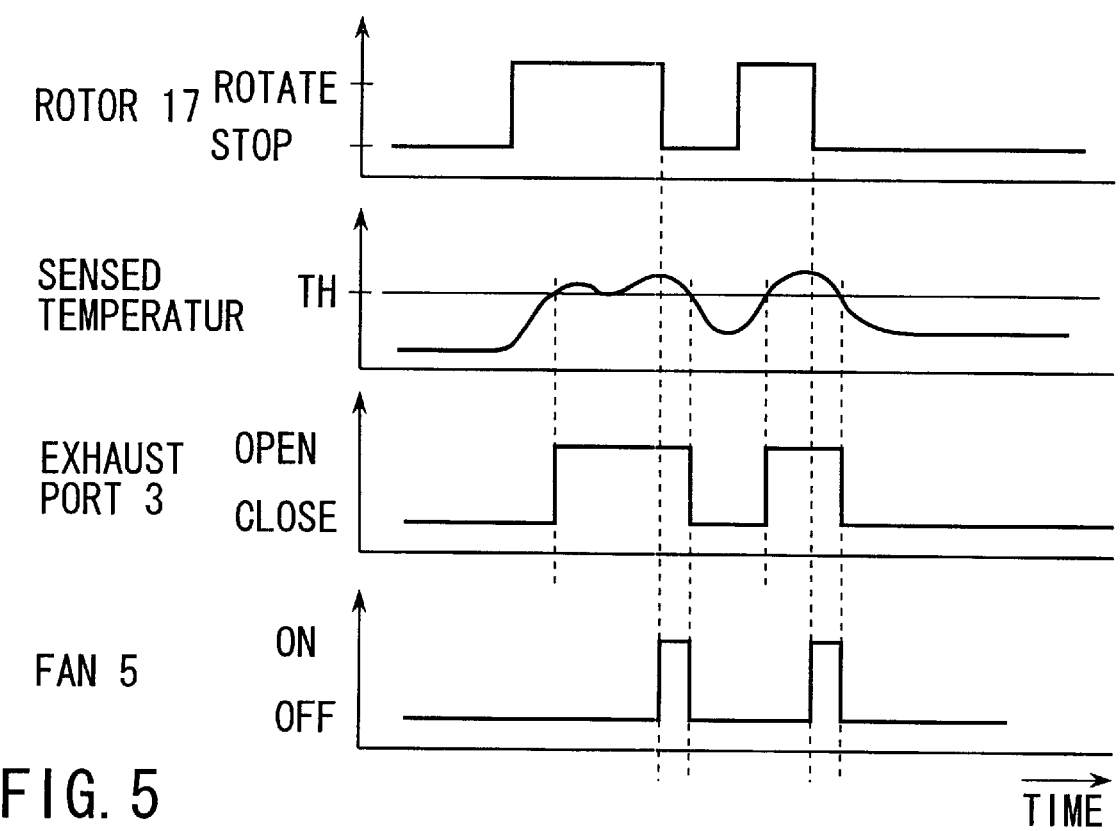
FIG. 5 is a view showing a control operation (open and close operation of an exhaust port and activation/deactivation of a ventilation fan) using a ventilation controller shown in FIG. 4.

As shown in FIG. 5, the rotor 17 is rotated intermittently together with scan execution and stoppage. In addition, the temperature inside of the cabinet of the gantry fluctuates due to a variety of factors such as X-ray exposure frequency. The ventilation controller 19 supervises the temperature inside of the cabinet based on the output of the temperature sensor 6. When the cabinet inside temperature exceeds a predetermined threshold value TH, the exhaust port 3 is opened. In this manner, the air inside of the cabinet is ventilated, and the temperature inside of the cabinet is lowered. On the other hand, when the cabinet inside temperature is lowered not more than a predetermined threshold TH, the exhaust port 3 is closed. In this manner, when the ventilation of the air inside of the cabinet is stopped, the lowering of the temperature inside of the cabinet is suppressed. Through such opening and closing control, the fluctuation of the temperature inside of the cabinet can be suppressed within a comparatively narrower range around the threshold value TH. In general, a semiconductor device such as photo diode of the X-ray detector 16 and electric circuit of a data acquisition unit (DAS) is sensitive to a temperature change. Functional degradation may occur if a temperature is too high or too low. As in the present embodiment, the internal temperature is not only lowered, but also is prevented from being excessively lowered, whereby the semiconductor device can be preferably operated.

In addition, the ventilation controller 19 supervises the temperature inside of the cabinet based on an output of a temperature sensor 6, and supervises activation/deactivation of the rotor 17 based on an output of a rotary encoder 10. Based on this supervision result, the activation/deactivation of the ventilation fan unit 5 is switched.

Specifically, when the temperature inside of the cabinet exceeds a predetermined threshold value TH, and moreover, the rotor 17 is deactivated, the ventilation fan unit 5 is operated. Then, the air inside of the cabinet is forcibly ventilated. On the other hand, when the rotor 17 is operated, even if the temperature inside of the cabinet exceeds a predetermined threshold value TH, the ventilation fan unit is deactivated. In addition, even when the rotor 17 is deactivated, when the temperature inside of the cabinet is lowered than the predetermined threshold value TH, the ventilation fan unit 5 is deactivated.

Namely, when the rotor 17 is rotated, or, when a scan (X-ray radiation and acquisition of projection data) is executed, the ventilation fan unit 5 is always deactivated. Forcible ventilation is performed only when the rotor 17 is deactivated or X-ray radiation is stopped, and moreover, the temperature inside of the cabinet exceeds the predetermined threshold value TH. Therefore, noise during scanning can be reduced to the minimum.

(Second Embodiment)

Now, a second embodiment of the present invention will be described here. Hereinafter, the points different from the first embodiment will be primarily described.

Figure 6:
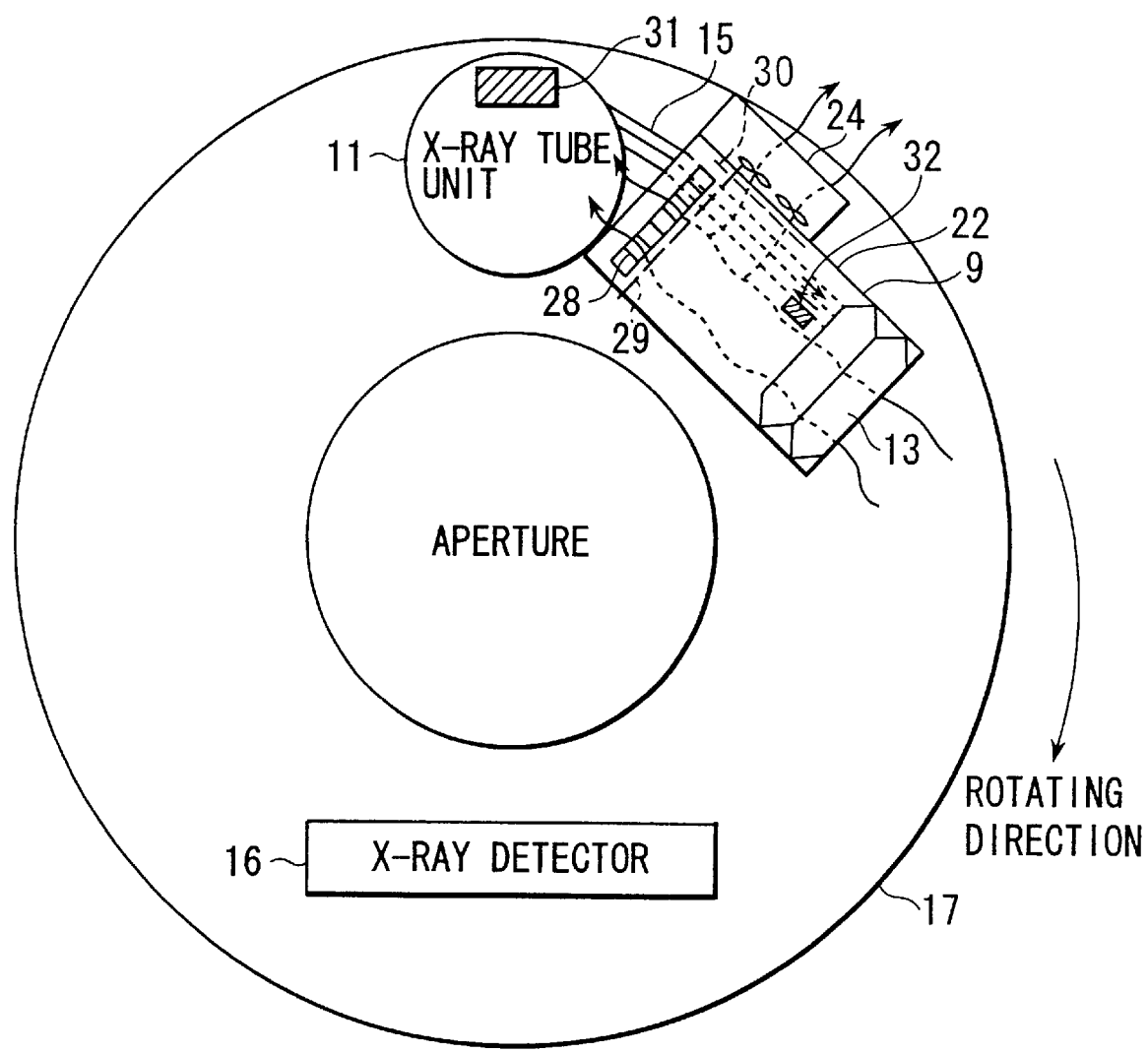
FIG. 6 is a structural view showing a rotation section inside a gantry of the X-ray computed tomography apparatus according to a second embodiment of the present invention.

FIG. 6 is a frontal view showing a rotor 27 inside of a gantry of an X-ray computed tomography apparatus according to the second embodiment. A radiator unit 22 according to the present embodiment is equipped with a fan unit 24. When this fan unit 22 operates, the quantity of air passing through the radiator 13 increases. The oil cooling effect is thus improved.

In addition, a opening and closing mechanism 29 is provided at the radiator unit 22 so as to enable a radiator air exit 28 to be opened/closed by being electrically driven. By means of the opening and closing mechanism 29, when the radiator air exit 28 is opened, air passes through the radiator 13 together with rotation of the rotor 17. When the radiator air exit 28 is closed by means of the opening and closing mechanism 29, even if the rotor 17 is rotated, the air hardly passes through the radiator 13. Thus, the oil cooling efficiency is reduced. Moreover, an opening and closing mechanism 30 may be provided at an air entrance or exit of the fan unit 24. When the mechanisms 29, 30 close the air exits, the reduction of the cooling efficiency is facilitated.

The fan unit 24 is activated/deactivated, and the radiator air exit 28 is opened or closed by means of the opening and closing mechanism 29, whereby the quantity of air passing through the radiator 13 can be accurately controlled.

The activation/deactivation of the fan unit 24 and the opening and closing of the radiator air exit 28 by means of the opening and closing mechanism 29 are controlled based on at least one of an output of a temperature sensor 31 mounted to the outer surface or the like of the X-ray tube in order to directly detect the temperature of the X-ray tube and an output of the temperature sensor 32 mounted to a hose 15 that circulates oil from the radiator 13 to the X-ray tube unit 11 in order to detect the temperature of the oil immediately after cooling, for example.

The temperature sensor 31 has characteristics sensitive to a temperature change in the X-ray tube because it detects the X-ray tube temperature. On the other hand, the temperature sensor 32 is comparatively sensitive to a temperature change in the X-ray tube because it detects a temperature of the circulation oil, but has characteristics sensitive to the cooling effect upon the radiator 13.

Figure 7:
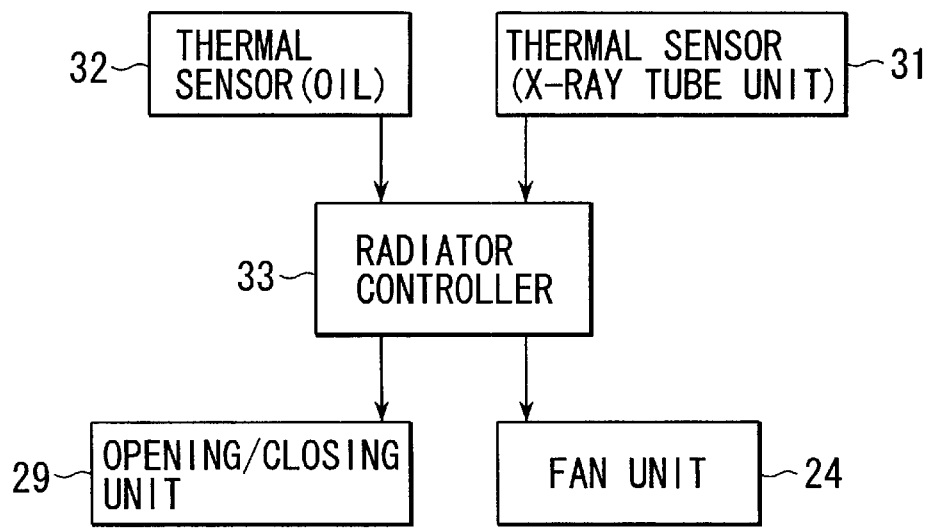
FIG. 7 is a block diagram depicting a radiator unit controlling system in the second embodiment.

FIG. 7 shows a control system of the radiator unit 22. The radiator controller 33 is provided at one section of the control unit for mainly controlling X-ray generation, the control unit being mounted to a rotor 17, for example. An output of the temperature sensor 31 and an output of the temperature sensor 32 are acquired by a radiator controller 33. The radiator controller 33 comprises three types of control modes for activation/deactivation of the fan unit 24 and opening and closing of the radiator air exit 28 by means of the opening and closing mechanism 29. The operator can select control mode arbitrarily.

Figure 8:
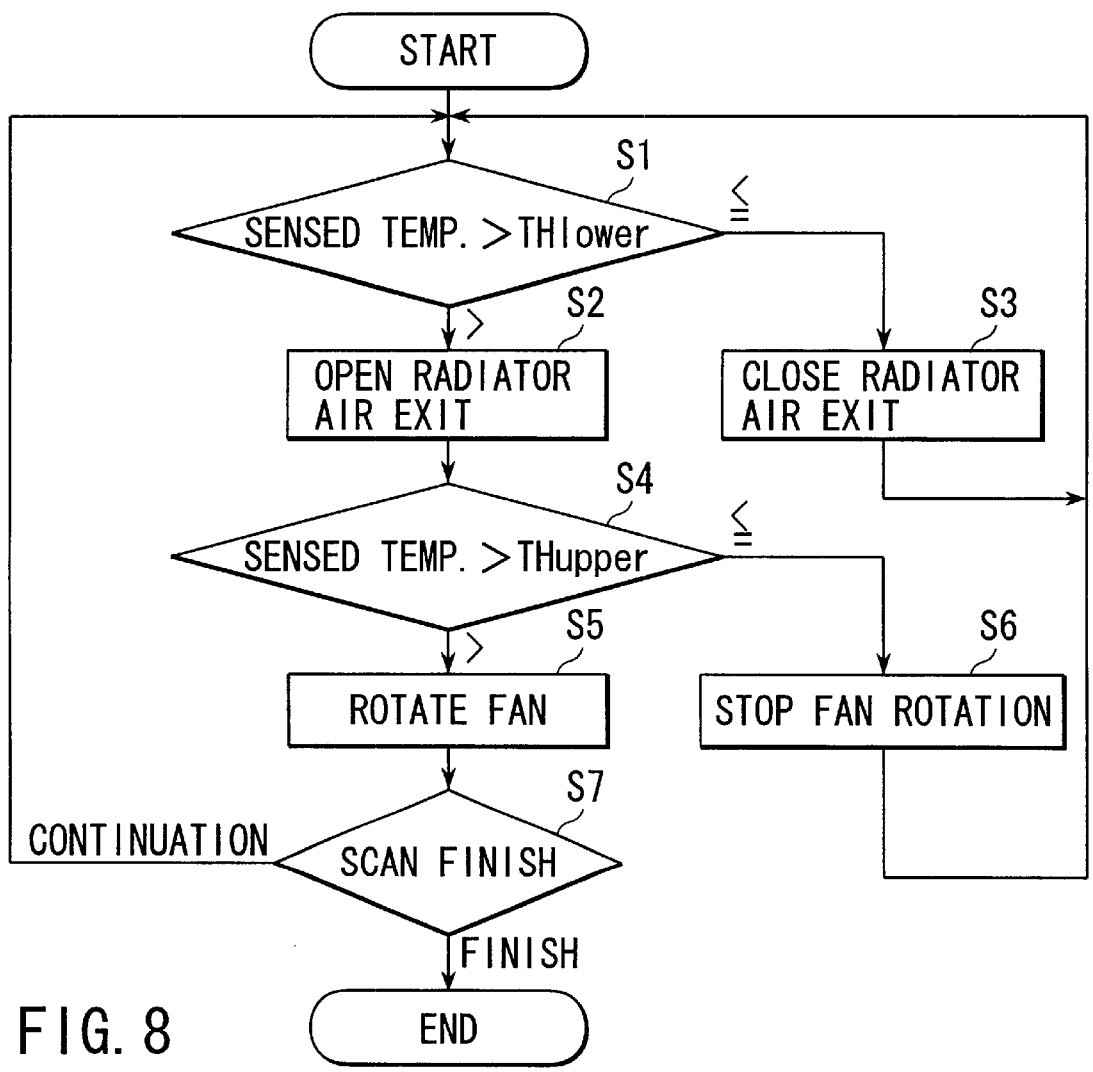
FIG. 8 is a view showing the steps of controlling the radiator unit controller shown in FIG. 7.
Figure 9:
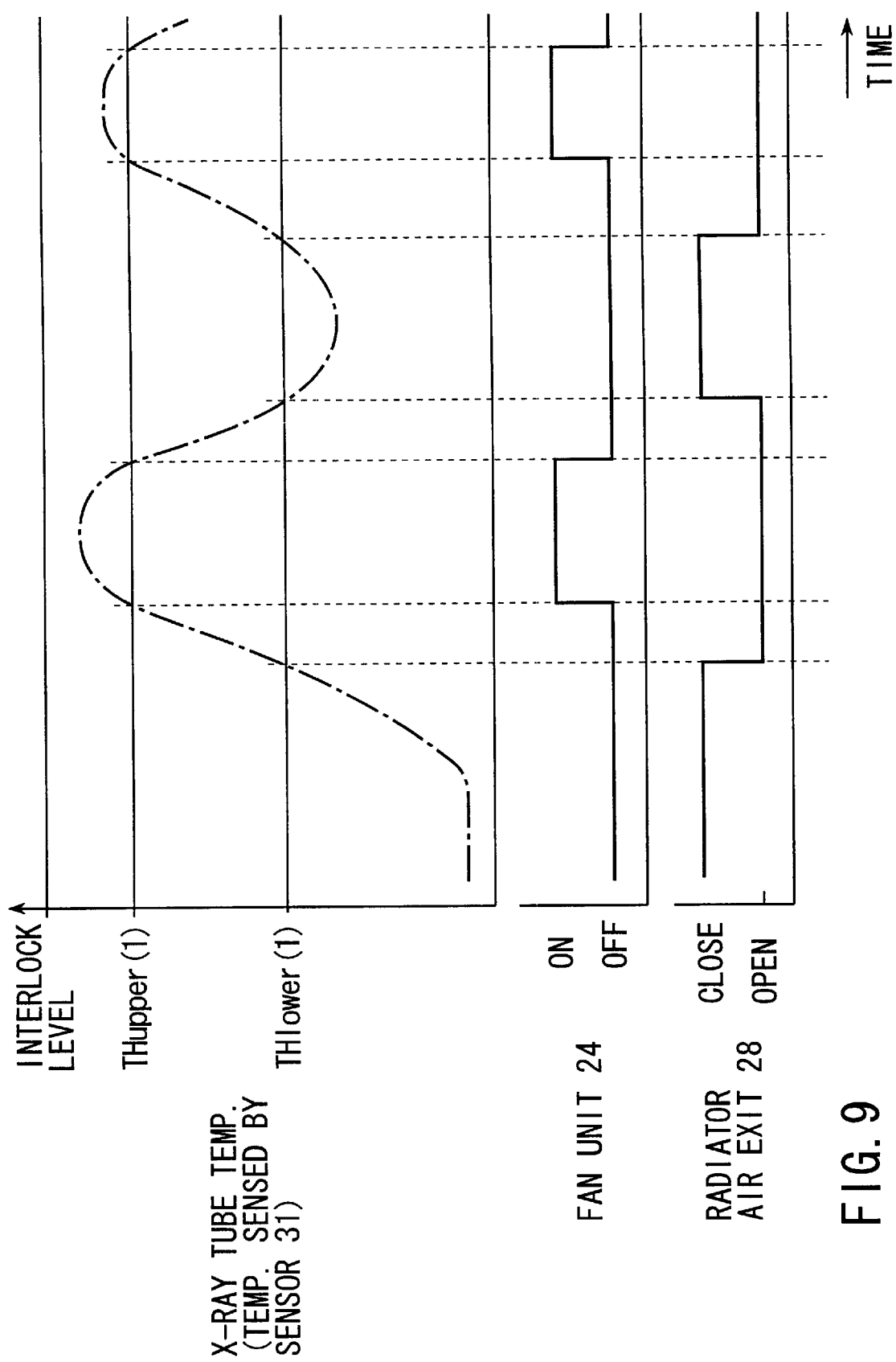
FIG. 9 is a view showing a control operation of the radiator unit controller (opening and closing of an radiator air exit and activation/deactivation of the fan) shown in FIG. 7 based on an output of the X-ray tube temperature sensor shown in FIG. 7.

FIG. 8 shows the steps of controlling first mode using the radiator controller 33. FIG. 9 shows a change in activation/deactivation of the fan unit 24 relative to a change in X-ray temperature (detection temperature of the sensor 31) and a change in opening and closing of the radiator air exit 28. In general, the upper limit value of the X-ray tube temperature is specified as an interlock level. When the X-ray tube temperature exceeds the interlock level, the supply of power (tube voltage or filament current) to the X-ray tube unit 11 is stopped urgently in order to urgently stop the X-ray generation. An upper threshold value TH upper (1) is set at a temperature lower than this interlock level. In addition, a lower threshold value TH lower (1) is set at a temperature slightly higher than a temperature at which the arcing in the X-ray tube is comparatively higher in frequency.

In the radiator controller 33, the X-ray tube temperature detected by the sensor 31 is compared with the lower threshold value TH lower (1) (S1), and the X-ray tube temperature detected by the sensor 31 is compared with the upper threshold value TH upper (1) (S4).

When the X-ray tube temperature is equal to or smaller than the lower threshold value TH lower (1), the radiator air exit 28 is closed in order to prevent excessive cooling (S3). On the other hand, when the X-ray tube temperature exceeds the lower temperature TH lower (1), the radiator air exit 28 is opened in order to improve the cooling effect of the radiator unit 22 (S2).

In addition, when the X-ray tube temperature exceeds the upper threshold value TH upper (1), a fan unit 24 is operated in order to improve the cooling capacity. On the other hand, when the X-ray tube temperature is equal to or smaller than the upper threshold value TH upper (1), the fan unit 24 is deactivated in order to prevent excessive cooling (S6). Such controlling is continued until radiography has been completed (S7).

Thus, with respect to a temperature rise, the radiator air exit 28 is first opened. Even in the case where such temperature rise cannot be stopped, the fan unit 24 is operated. In addition, with respect to a temperature fall, the fan unit 24 is deactivated. Even in the case where such temperature fall cannot be stopped, the radiator air exit 28 is closed.

When rotation of the rotor 17 is stopped, and when the X-ray tube temperature exceeds the upper threshold value TH upper (1), the radiator air exit 28 is closed in order to obtain the cooling effect, and the fan unit 24 is operated.

Figure 10:
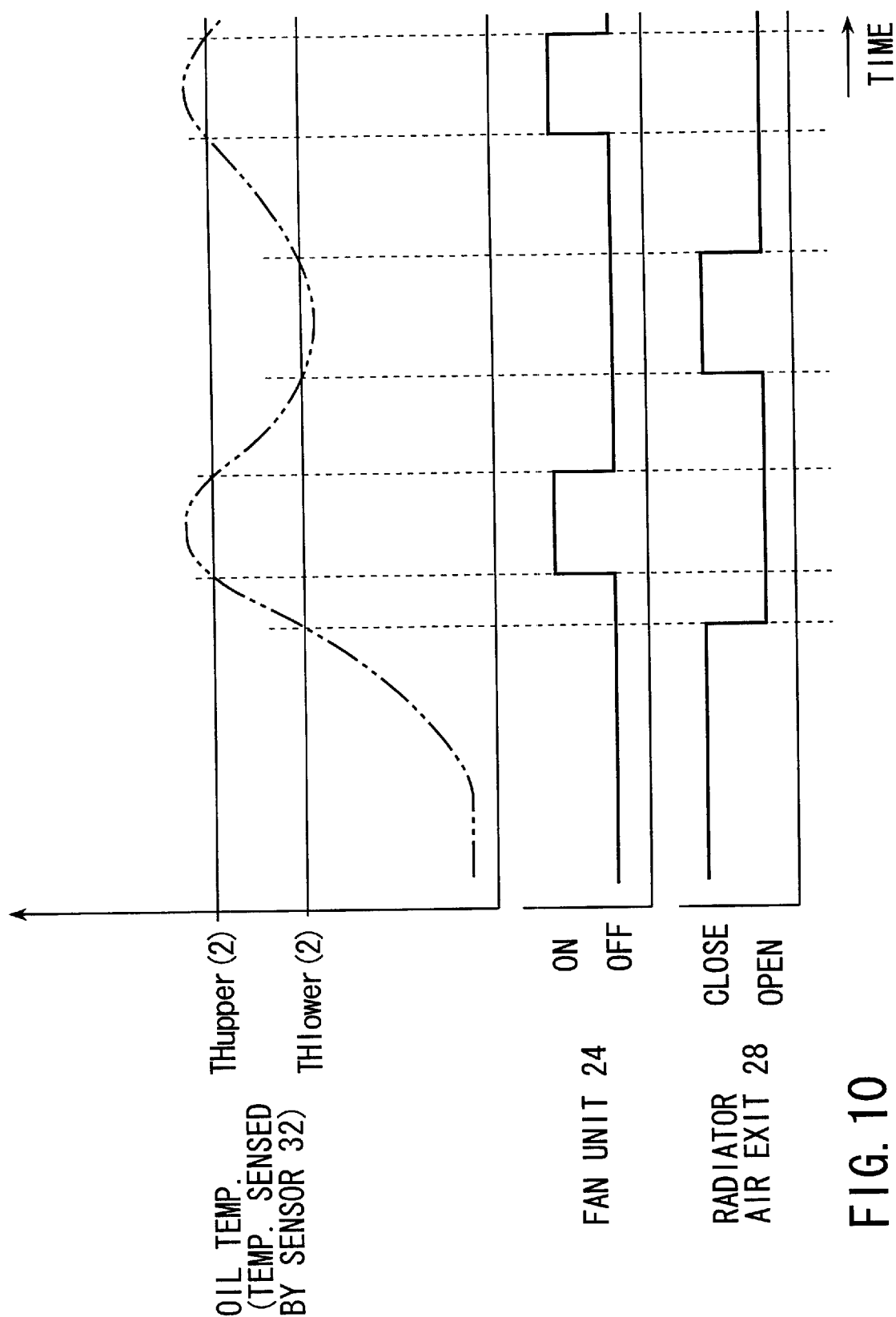
FIG. 10 is a view showing a control operation of the radiator unit controller (opening and closing of an radiator air exit and activation/deactivation of the fan) shown in FIG. 7 based on an output of the oil temperature sensor shown in FIG. 7.

In FIG. 10, in a second mode of the radiator controller 33, there is shown a change in activation/deactivation of the fan unit 24 relevant to a change in oil temperature (temperature detected by the sensor 32) and a change in opening and closing of the radiator air exit 28. The upper threshold value TH upper (2) relevant to the oil temperature may be set at a temperature lower than the upper threshold value (1) relevant to the X-ray tube temperature used in a first mode. Similarly, the lower threshold value TH lower (2) relevant to the oil temperature is set at a temperature higher than the lower threshold value TH lower (1) relevant to the X-ray tube temperature used in the first mode.

In the radiator controller 33, as in the first mode, the oil temperature detected by the sensor 32 is compared with the lower threshold value TH lower (2), and the oil temperature detected by the sensor 32 is compared with the upper threshold value TH upper (2). When the oil temperature is equal to or smaller than the lower threshold value TH lower (2), the radiator air exit 28 is closed in order to prevent excessive cooling. On the other hand, when the oil temperature exceeds the lower threshold value TH lower (2), the radiator air exit 28 is opened. In addition, when the oil temperature exceeds the upper threshold value TH upper (2), the fan unit 24 is operated. On the other hand, when the oil temperature is equal to or smaller than the upper threshold value TH upper (2), the fan unit 24 is deactivated in order to excessive cooling.

When the rotor 17 is deactivated, and when the oil temperature exceeds the upper threshold value TH upper (2), the radiator air exit 28 is closed in order to obtain the cooling effect, and the fan unit 24 is operated.

Figure 11:
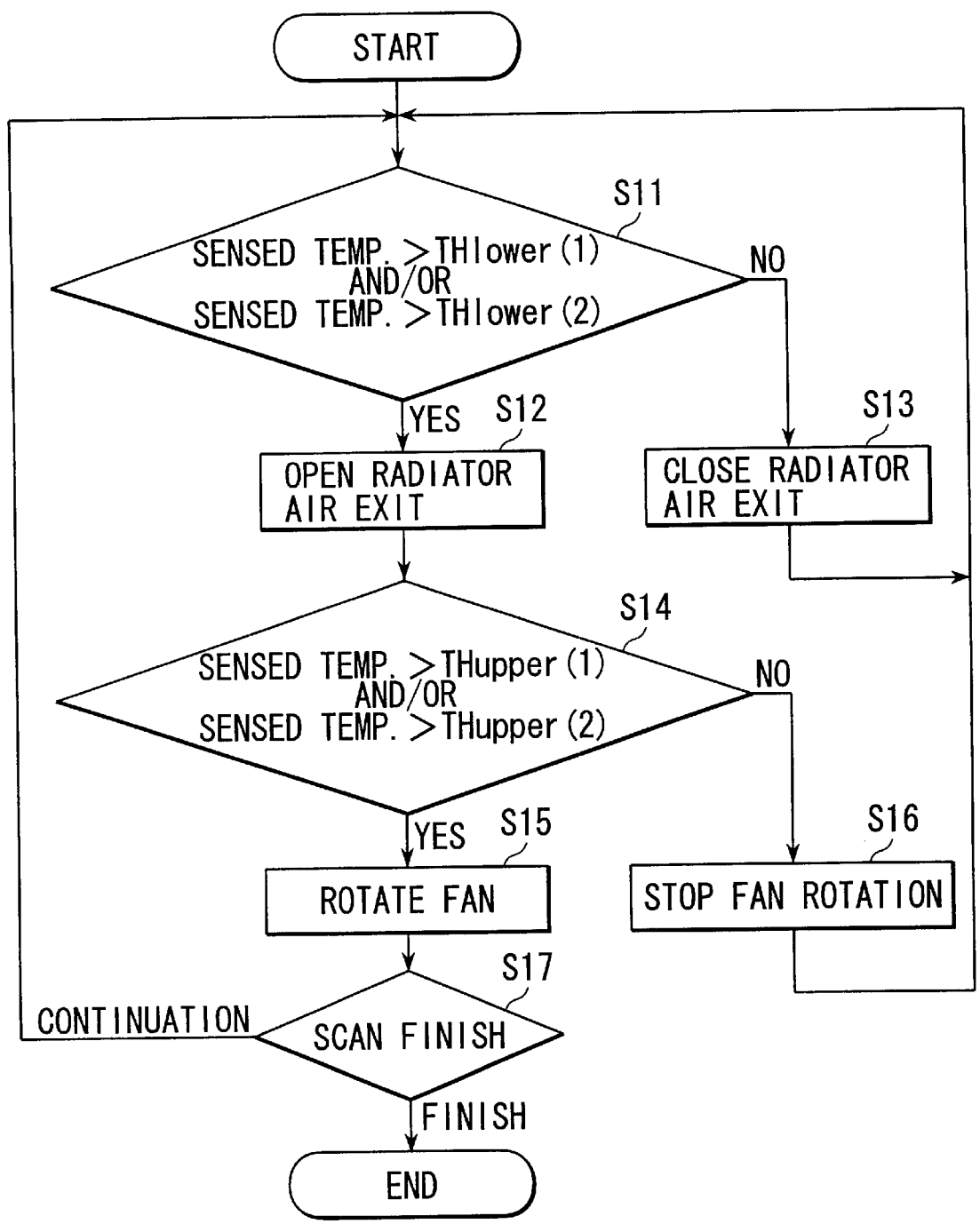
FIG. 11 is a view showing the steps of controlling the radiator unit controller based on both of the output of the X-ray tube temperature sensor shown in FIG. 7 and the output of the oil temperature sensor.
Figure 12:
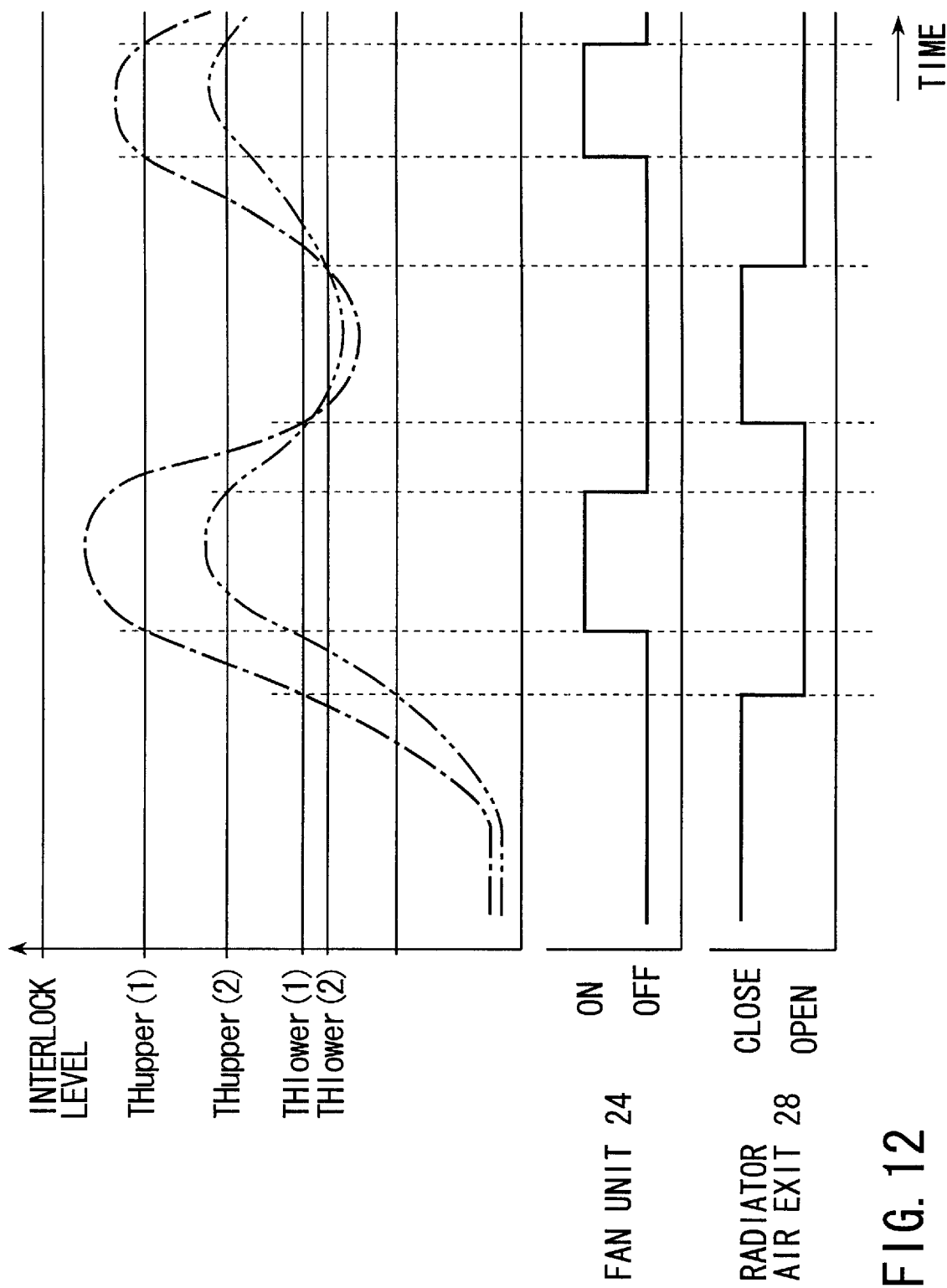
FIG. 12 is a view showing a control operation of the radiator unit controller (opening and closing of the radiator air exit and activation and deactivation of the fan) shown in FIG. 7 based on both of the output of the X-ray tube temperature sensor and the output of the oil temperature sensor shown in FIG. 7.

In a third mode, controlling is performed by using both of two types of sensors 31 and 32. FIG. 11 shows the steps of controlling the third mode using the radiator controller 33. FIG. 12 shows a change in activation/deactivation of the fan unit 24 relevant to a change in X-ray tube temperature (temperature detected by the sensor 31) and a change in oil temperature (temperature detected by the sensor 32); and a change in opening and closing of the radiator air exit. In the radiator controller 33, the X-ray tube temperature detected by the sensor 31 is compared with the lower threshold value lower (1), and the oil temperature detected by the sensor 32 is compared with the lower threshold value TH lower (2) (S11). Here, when at least one of the X-ray tube temperature and the oil temperature exceeds each one of the lower threshold values TH lower (1) and TH lower (2), the radiator air exit 28 is opened in order to improve the cooling effect of the radiator unit 22 (S22). On the other hand, when both of the X-ray tube temperature and the oil temperature are equal to or smaller than the respective lower threshold values TH lower (1) and TH lower (2), the radiator air exit 28 is closed in order to prevent excessive cooling (S13).

In addition, in the radiator controller 33, the X-ray tube temperature is compared with the upper threshold value TH upper (1), and the oil temperature is compared with the upper threshold value TH upper (2) (S14). Here, when at least one of the X-ray tube temperature and the oil temperature exceeds each one of the threshold values TH upper (1) and TH upper (2), the fan unit 22 is operated (Si5). On the other hand, when both of the X-ray tube temperature and the oil temperature are equal to or smaller than the respective upper threshold values TH upper (1) and TH upper (2), the fan unit 22 is deactivated in order to prevent excessive cooling (S16). Such controlling is continued until radiography has been completed (S17). When rotation of the rotor 17 is stopped, and when at least one of the X-ray tube temperature and the oil temperature exceeds the upper threshold value, the radiator air exit 28 is closed in order to obtain the cooling effect, and the fan unit 24 is operated.

According to the present embodiment, the temperature can be controlled with higher precision than that in the first embodiment.

In the foregoing description, although the activation/deactivation of the fan unit 24 is switched, the quantity of air from the fan unit 24 may be finely adjusted. Namely, a plurality of upper threshold values are set in stepwise manner. At a temperature rise, the air quantity of the fan unit 24 is increased in stepwise manner every time the quantity exceeds each of the upper threshold values. On the other hand, at a temperature fall, the air quantity of the fan unit 24 is reduced in stepwise manner every time the quantity is smaller than each of the upper threshold values. The air quantity may be adjusted by increasing or decreasing the number of fans to be driven, and its output may be changed by changing the power applied to the fan unit 24.

(Third Embodiment)

Figure 13:
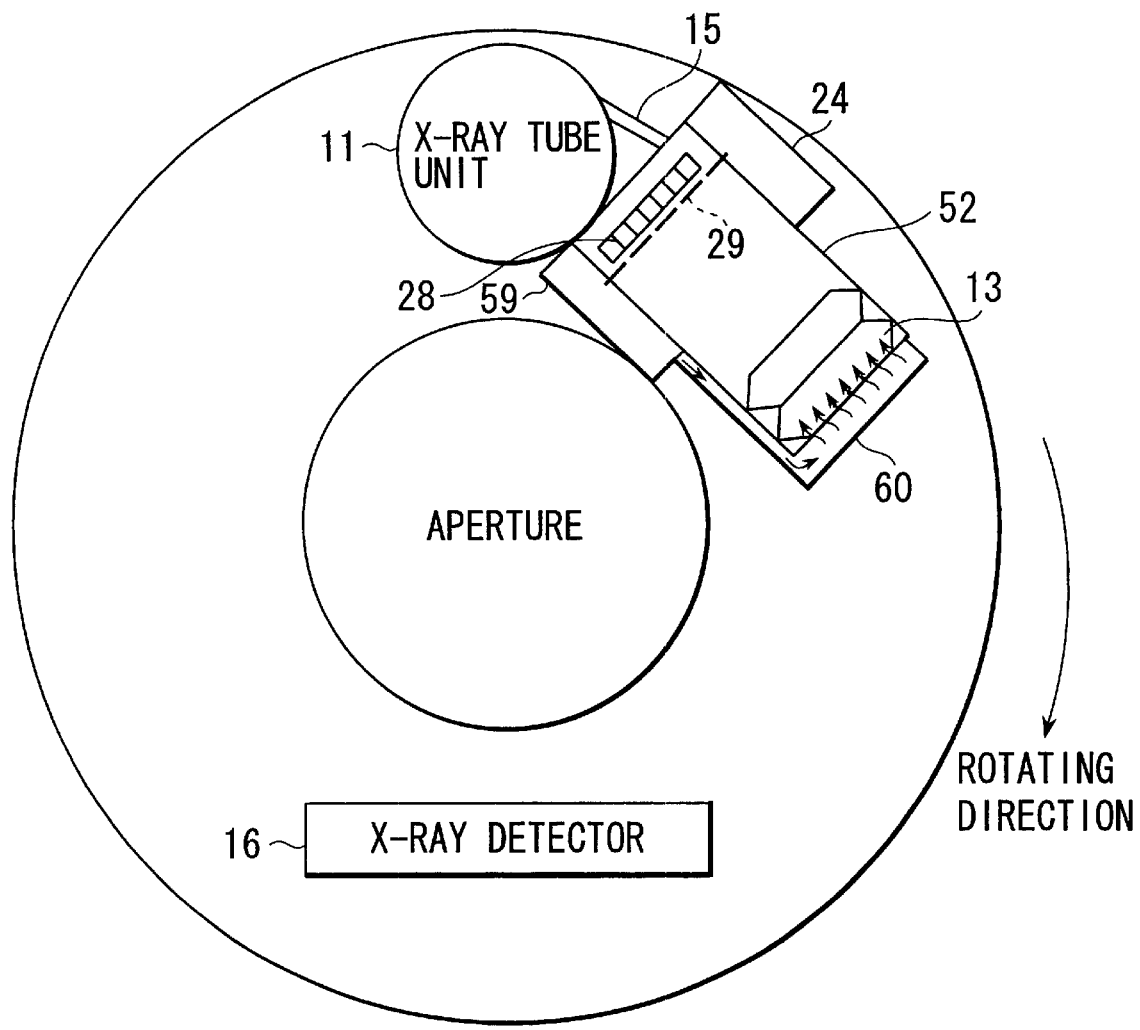
FIG. 13 is a structural view showing a rotation section inside of a gantry of an X-ray computed tomography apparatus according to a third embodiment of the present invention.

Now, a third embodiment of the present invention will be described here. FIG. 13 is a front view showing a rotor 17 inside of a gantry of an X-ray computed tomography apparatus in the third embodiment. A radiator unit 52 according to the present embodiment is equipped with a cooler (cooling unit) 59 in addition to an arrangement of the radiator unit according to the second embodiment. The cooler 59 has a coolant vaporization—liquefying cycle system, and a vaporizer 60 is disposed in front of the radiator 13. When the cooler 59 is operated, the air cooled at a temperature less than the internal temperature of the gantry is supplied to the radiator 13 by means of the vaporizer 60. In this manner, the oil cooling effect is significantly improved.

Figure 14:
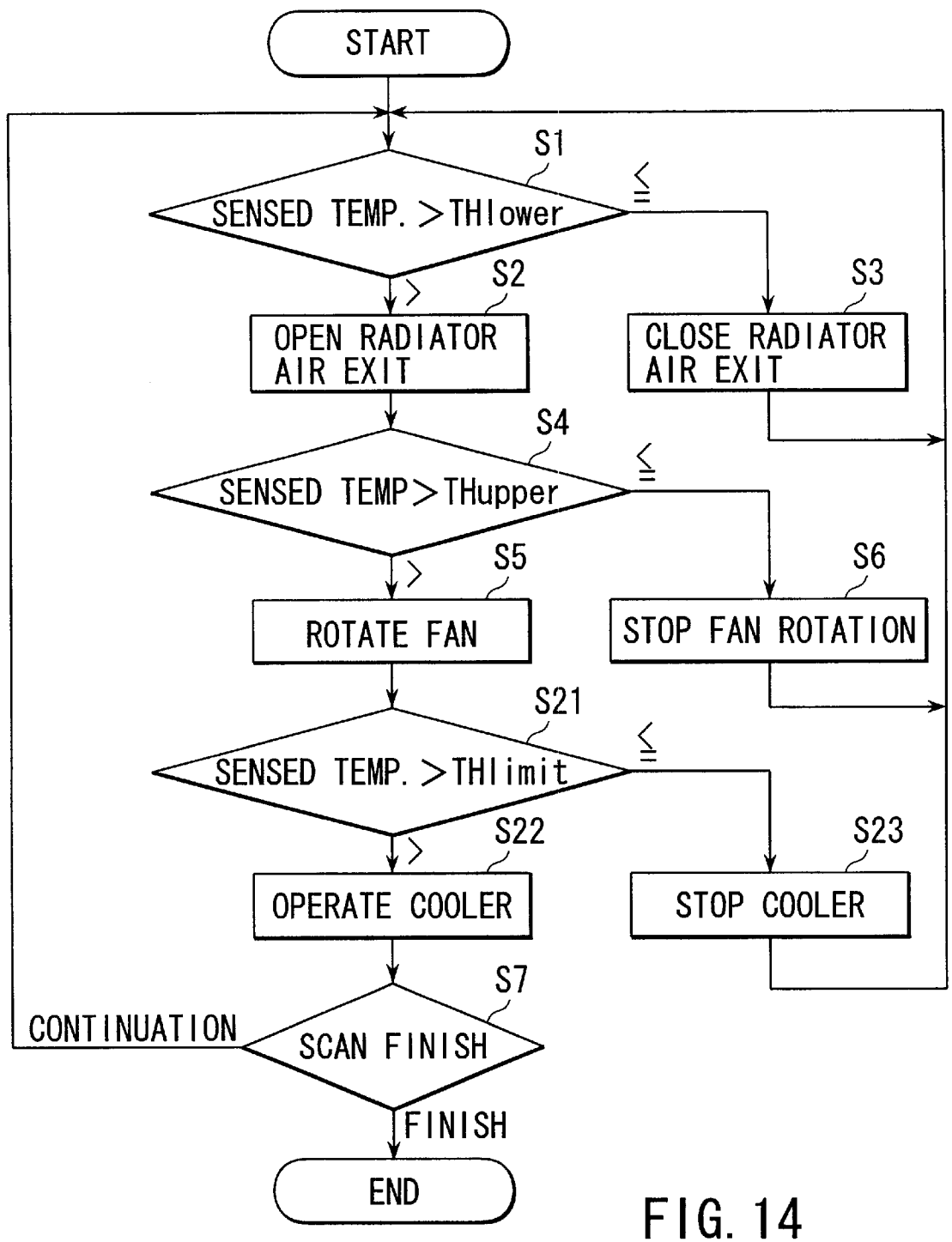
FIG. 14 is a view showing the steps of controlling a radiator unit controller according to the third embodiment.
Figure 15:
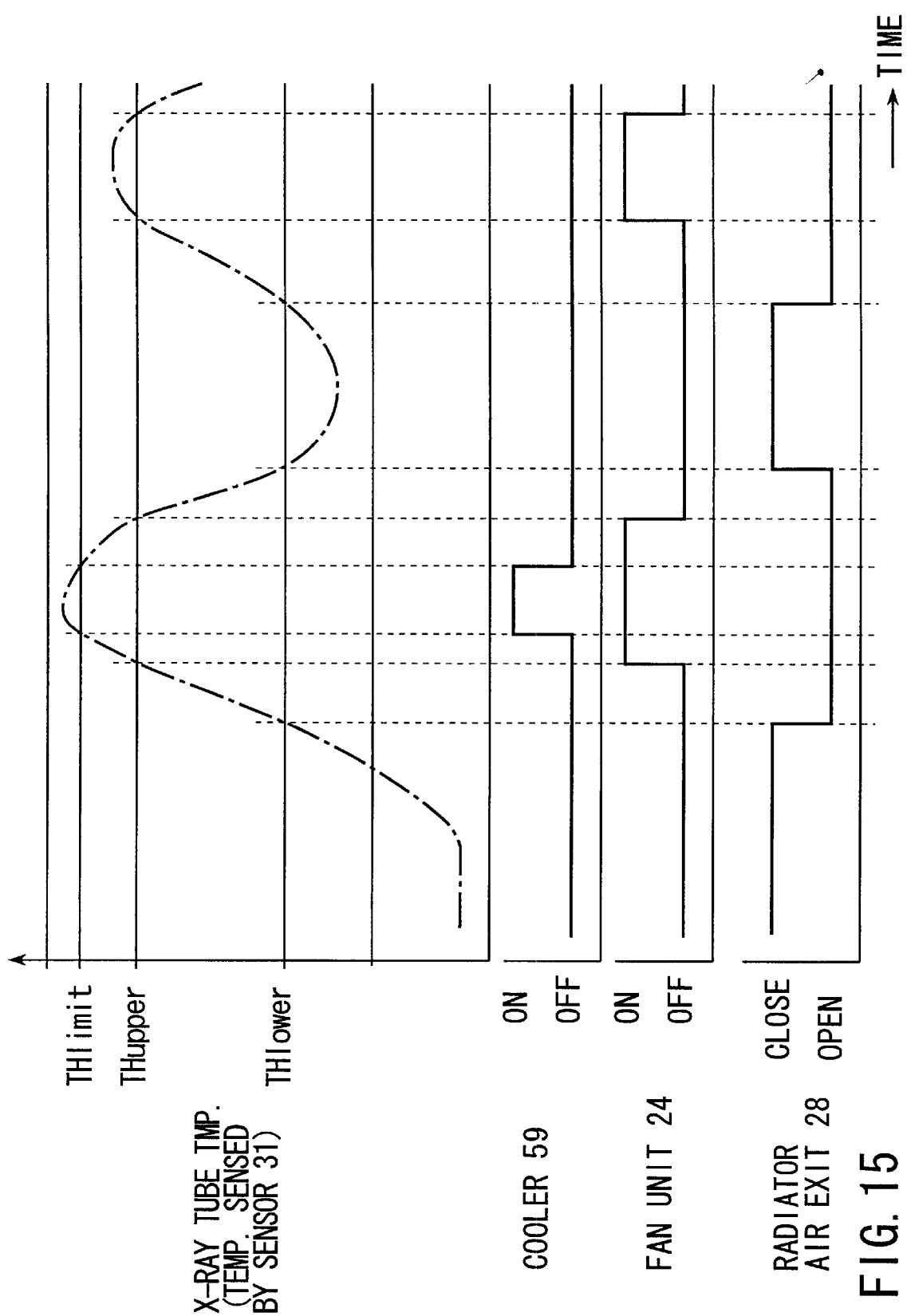
FIG. 15 is a view showing a control operation of the radiator unit controller according to the third embodiment (opening and closing of the radiator air exit, activation/deactivation of the fan, and activation/deactivation of a cooler).

FIG. 14 shows the control steps using the radiator controller. FIG. 15 shows an example when the activation/deactivation of the fan unit 24 is switched relevant to a change in x-ray tube temperature (temperature detected by the sensor 31); when the radiator air exit 28 is opened and closed; and the activation/deactivation of the cooler 59 is switched. Although the control operation of the present embodiment will be described here based on the first mode of the second embodiment, it is applicable to the second mode and the third mode.

The control operation of the present embodiment is different from that of the second embodiment as follows. That is, the upper limit value TH limit is set between an interlock level and an upper threshold value TH upper; the X-ray tube temperature is compared with the upper limit TH limit (S21); when the X-ray tube temperature exceeds the upper limit TH limit, the cooler 59 is operated in order to cool the oil accurately (S22); and when the X-ray tube temperature is lowered to be equal to or smaller than the upper limit value TH limit, the cooler 59 is deactivated in order to prevent excessive cooling (S23).

In this embodiment, although only activation/deactivation of the cooler 59 is switched, the cooling capability of the cooler 59 may be finely adjusted. Namely, a plurality of upper limits TH limit is set in stepwise manner. At a temperature rise, the output of the cooler 59 is increased in stepwise manner every time the output exceeds each of the upper limits. On the other hand, at a temperature fall, the output of the cooler 59 is decreased in stepwise manner every time the output is lower than each of the upper limits.

According to the present embodiment, the X-ray tube temperature can be reduced by means of the cooler 59. Thus, the apparatus is suitable to a case of scanning a large number of persons in which longer X-ray exposure time is required. In addition, in the case where the X-ray tube temperature rises abnormally, and an interlock is provided, the X-ray tube temperature is decreased rapidly, and a state in which X-ray exposure is possible can be restored within a short period of time.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomography apparatus comprising:
a rotor rotated in a predetermined direction;
an X-ray tube unit mounted on said rotor;
an X-ray detector opposed to said X-ray tube unit to detect X-ray transmitted through a subject; and
a radiator unit mounted on said rotor,
wherein:
said radiator unit comprises a tubed casing, a radiator engaged with a frontal opening of said casing in an orientation in which the radiator is subjected to the air moved by rotation of said rotor at a substantial front face thereof, a circulating system configured to circulate a fluid between said X-ray tube unit and said radiator, and a radiator air exit opened at the rear of said casing; and
said radiator unit further comprises a switch for opening and closing said radiator air exit.

2. An X-ray computed tomography apparatus according to claim 1, wherein said apparatus further comprises a controller for controlling said switch so that at least one of an X-ray tube unit temperature and a fluid temperature is maintained at a predetermined temperature or more.

3. An X-ray computed tomography apparatus according to claim 1, wherein said apparatus further comprises a controller for controlling said switch so as to open said radiator air exit when at least one of an X-ray tube unit temperature and a fluid temperature exceeds a predetermined threshold value, and to close said radiator air exit when at least one of said X-ray tube unit temperature and said fluid temperature is lowered less than said threshold value.

4. An X-ray computed tomography apparatus according to claim 1, wherein said radiator unit further comprises a fan unit for forcibly exhausting the air in said casing.

5. An X-ray computed tomography apparatus according to claim 4, wherein said apparatus further comprises a controller for controlling said switch and said fan unit so that at least one of an X-ray tube unit temperature and a fluid temperature is maintained at a predetermined temperature or more.

6. An X-ray computed tomography apparatus according to claim 4, wherein said apparatus further comprises a controller for controlling said switch to open said radiator air exit when at least one of an X-ray tube unit temperature and a fluid temperature exceeds a lower threshold value and to close said radiator air exit when at least one of said X-ray tube unit temperature and said fluid temperature is equal to or smaller than said lower threshold value; and for controlling said fan unit to be activated when at least one of said X-ray tube unit temperature and said fluid temperature exceeds an upper threshold value; and to be deactivated when at least one thereof is equal to or smaller than said upper threshold value.

7. An X-ray computed tomography apparatus according to claim 4, wherein said radiator unit further comprises a cooler unit for supplying cooling air to said radiator.

8. An X-ray computed tomography apparatus according to claim 4, wherein said apparatus further comprises a controller for controlling said switch to open said radiator air exit when at least one of an X-ray tube unit temperature and a fluid temperature exceeds a lower threshold value and to close said radiator air exit when at least one of said X-ray tube unit temperature and said fluid temperature is equal to or smaller than said lower threshold value; and for controlling said cooler unit to be activated when at least one of said X-ray tube unit temperature and said fluid temperature is set to be higher than said upper threshold value and to be deactivated when at least one of said X-ray tube unit temperature and said fluid temperature is equal to or smaller than said upper threshold value.

9. An X-ray computed tomography apparatus according to claim 1, wherein said radiator unit further comprises an air filter engaged with said radiator air exit.

10. An X-ray computed tomography apparatus comprising:
a gantry cabinet;
a rotor stored in said gantry cabinet and rotated in a predetermined direction;
an x-ray tube unit mounted on said rotor;
an x-ray detector mounted on said rotor so as to be opposed to said X-ray tube unit;
an exhaust port provided at said gantry cabinet;
an air intake port provided at said gantry cabinet;
a ventilation fan unit provided at least at one of said exhaust port and said air intake port; and
a controller configured to control said ventilation fan unit to be activated when said rotor is deactivated, and to be deactivated when said rotor is activated,
wherein said apparatus further comprises a switch for opening and closing said exhaust port.

11. An X-ray tomography apparatus according to claim 10, wherein said controller controls said switch to close said exhaust port when the internal temperature of said gantry cabinet is equal to or smaller than a predetermined temperature.

12. An X-ray computed tomography apparatus comprising:
an X-ray tube unit configured to generate X-rays with rotating around a subject;
a cooling unit configured to cool said X-ray tube unit;
an x-ray detector configured to detect X-rays transmitted through the subject;
a gantry cabinet configured to house said X-ray tube unit, said cooling unit and said X-ray detector;
a ventilation system configured to ventilate an air inside of said gantry cabinet; and
a control unit configured to control said ventilation system with said cooling unit based on at least one of a temperature inside of said gantry cabinet, an X-ray generating condition of said X-ray tube unit and a rotating condition of said X-ray tube unit,
wherein said ventilation system includes an exhaust port and an air intake port provided to said gantry cabinet, and a mechanism for opening/closing said exhaust port and/or said air intake port.

13. An X-ray computed tomography apparatus according to claim 12, wherein said ventilation system includes a ventilator provided at said exhaust port or said air intake port.

14. An X-ray computed tomography apparatus according to claim 12, wherein said cooling unit includes a radiator and a circulating system configured to circulate a fluid between said X-ray tube unit and said radiator.

15. An X-ray computed tomography apparatus according to claim 1, wherein said radiator is disposed at a position more frontal than said X-ray tube unit in the rotational direction of said rotor.

16. An X-ray computed tomography apparatus according to claim 1, wherein said radiator is disposed so that a vertical line of its face is substantially parallel to a tangent line at a position of said radiator of a circle around a rotary shaft of said rotor.

* * * * *